US010751264B2

(12) United States Patent
Craig et al.

(10) Patent No.: US 10,751,264 B2
(45) Date of Patent: Aug. 25, 2020

(54) CURABLE COMPOSITIONS AND METHODS FOR ISOLATING A WORKING AREA

(71) Applicant: 3M INNOVATIVE PROPERTIES COMPANY, St. Paul, MN (US)

(72) Inventors: Bradley D. Craig, Lake Elmo, MN (US); Joel D. Oxman, Minneapolis, MN (US); Thomas P. Klun, Lakeland, MN (US); Richard B. Ross, Cottage Grove, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 547 days.

(21) Appl. No.: 15/315,530

(22) PCT Filed: Jun. 8, 2015

(86) PCT No.: PCT/US2015/034654
§ 371 (c)(1),
(2) Date: Dec. 1, 2016

(87) PCT Pub. No.: WO2015/191436
PCT Pub. Date: Dec. 17, 2015

(65) Prior Publication Data
US 2017/0135911 A1    May 18, 2017

Related U.S. Application Data

(60) Provisional application No. 62/012,019, filed on Jun. 13, 2014, provisional application No. 62/095,113, filed on Dec. 22, 2014.

(51) Int. Cl.
| | |
|---|---|
| *A61C 5/82* | (2017.01) |
| *A61K 6/896* | (2020.01) |
| *C08G 77/442* | (2006.01) |
| *C08L 83/10* | (2006.01) |
| *A61K 6/18* | (2020.01) |
| *A61K 6/887* | (2020.01) |

(52) U.S. Cl.
CPC .............. *A61K 6/896* (2020.01); *A61C 5/82* (2017.02); *A61K 6/18* (2020.01); *A61K 6/887* (2020.01); *C08G 77/442* (2013.01); *C08L 83/10* (2013.01)

(58) Field of Classification Search
CPC ........ A61C 5/82; A61K 6/093; A61K 6/0011; A61K 6/083; C08G 77/442; C08L 83/10
See application file for complete search history.

(56) References Cited

U.S. PATENT DOCUMENTS

| | | |
|---|---|---|
| 3,050,491 A | 8/1962 | Siegfried |
| 4,071,424 A | 1/1978 | Dart |
| 5,258,437 A | 11/1993 | Takeuchi |
| 5,475,124 A | 12/1995 | Mazurek |
| 5,501,727 A | 3/1996 | Wang |
| 5,545,676 A | 8/1996 | Palazzotto |
| 5,639,445 A * | 6/1997 | Curtis ............... A61C 19/063 106/35 |
| 5,693,689 A | 12/1997 | Gibbon |
| 6,030,606 A | 2/2000 | Holmes |
| 6,305,936 B1 * | 10/2001 | Jensen ............... A61K 6/0011 433/136 |
| 6,441,118 B2 | 8/2002 | Sherman |
| 6,534,615 B2 | 3/2003 | Schafer |
| 7,371,782 B2 * | 5/2008 | Stannard ............... A61K 6/083 522/171 |
| 7,501,184 B2 | 3/2009 | Leir |
| 7,789,662 B2 * | 9/2010 | Van Eikeren ........... A61C 5/90 433/136 |
| 8,501,834 B2 * | 8/2013 | Maletz ............... A61K 6/083 522/13 |
| 9,326,917 B2 * | 5/2016 | Maletz ............... A61K 6/0011 |
| 2003/0083400 A1 * | 5/2003 | Jia ............... A61K 6/083 523/116 |
| 2003/0166740 A1 | 9/2003 | Mitra |
| 2003/0190584 A1 | 10/2003 | Heasley |
| 2003/0195273 A1 | 10/2003 | Mitra |
| 2004/0161724 A1 * | 8/2004 | Stannard ............... A61K 6/0011 433/136 |
| 2005/0250868 A1 | 11/2005 | Suzuki |
| 2005/0266378 A1 | 12/2005 | Heasley |
| 2006/0057541 A1 | 3/2006 | Kahwaty |
| 2010/0152296 A1 * | 6/2010 | Marmarinos ........ A61K 6/0011 514/576 |
| 2012/0101184 A1 | 4/2012 | Wang |
| 2012/0149800 A1 | 6/2012 | Lewandowski |
| 2013/0109777 A1 | 5/2013 | Eckert |

FOREIGN PATENT DOCUMENTS

| | | |
|---|---|---|
| EP | 0173567 | 3/1986 |
| WO | WO 1992-16593 | 10/1992 |
| WO | WO 2013-127989 | 9/2013 |
| WO | WO 2015-034692 | 3/2015 |

OTHER PUBLICATIONS

Belmares, "Hildebrand and Hansen Solubility Parameters from Molecular Dynamics with Applications to Electronic Nose Polymer Sensors"; J. Comp. Chem., 2004, vol. 25, No. 15, pp. 1814-1826.
International Search report for PCT International Application No. PCT/US2015/034654 dated Aug. 10, 2015, 4 pages.

* cited by examiner

*Primary Examiner* — Ralph A Lewis
(74) *Attorney, Agent, or Firm* — 3M IPC

(57) ABSTRACT

The present application is directed to a curable composition and a method for isolating a working area in a patient's mouth. The curable composition can include a borate-crosslinked polysiloxane, at least one ethylenically unsaturated monomer comprising at least two polymerizable groups, and an initiator.

20 Claims, No Drawings

CURABLE COMPOSITIONS AND METHODS FOR ISOLATING A WORKING AREA

FIELD

The present application is directed to a curable composition and a method for isolating a working area in the mouth to be treated and producing a shield for the surrounding gums and/or adjacent teeth.

BACKGROUND

With some dental treatments, aggressive chemical substances are used in the mouth which can cause burning to the oral mucosa. For example, acid etching techniques in dental surgery, applying a composite filling, and bleaching with preparations containing a high percentage of peroxide are used. Furthermore, certain preparations and restorative techniques are detrimentally impacted by the presence of saliva, blood, and other fluid which may be present and/or arise during the course of a given preparation or technique. It is therefore desirable to create a barrier to these fluids and leave the preparation area clean.

During the acid etching technique the dental enamel is treated with a highly-concentrated, phosphoric acid solution or gel within a prepared tooth cavity to improve the adhesion before the application of a primer and/or bonding. The phosphoric acid solution or gel is then left to act for approximately 20 seconds on the dental enamel. When such procedures are performed in the vicinity of the gum or an adjacent tooth, it is necessary to isolate the treatment area and shield the adjacent tissues from the etching means. It is further desirable to protect the treated tooth, or similarly a plurality of teeth, relative to the surrounding tissue of the oral cavity as best as possible, to prevent, for example blood or saliva from reaching the treated tooth.

During a whitening treatment, bleaching agents with a content of up to 35 wt. % hydrogen peroxide are directly applied onto the surface of the tooth or teeth. In some instances, the bleaching agent is applied up to the vicinity of the gum margin. It is important to isolate the treatment area and protect the oral mucosa from being burned by the bleaching agent.

Currently, shielding is accomplished by using a resilient sheet made from rubber which is referred to as a dental dam. In its original and simplest form, it consists of an elastic, flat covering means, mostly in the form of a rubber cloth, which may be fastened in a frame outside the mouth. The dentist then has to perforate the sheet at suitable points and punch out holes of a corresponding size in the sheet, through which the teeth to be treated are subsequently pushed. Where the size of the holes is unsuitable or where there are imperfections on the surface of the tooth, the problem frequently arises that the resilient sheet does not sit and seal precisely or tightly enough along the gum margin and thus does not sufficiently protect the oral mucosa. The positioning of a dental dam is regarded by many dentists as too costly and awkward. In addition, the dental dam may be time consuming to use. The danger arises that when stretched or during the treatment the rubber tears or loosens. As a result the isolating effect of the dental dam is lost and the material (for example, blood, saliva, and/or other fluids) present on the exterior of the rubber sheet can enter the working area. Additionally, patients find the equipment cumbersome and the fastening of the rubber on the neck of the tooth uncomfortable.

SUMMARY

Some aspects of the present disclosure provide a curable composition. The curable composition can include a borate-crosslinked polysiloxane, at least one ethylenically unsaturated monomer comprising at least two polymerizable groups, and an initiator.

Some aspects of the present disclosure provide a method for isolating a working area in a patient's mouth. The method can include providing the curable composition of the present application, molding the composition to provide a moldable isolation device having a desired shape, positioning the isolation device inside the patient's mouth to isolate the desired working area, and curing the isolation device.

Other features and aspects of the present disclosure will become apparent by consideration of the detailed description.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

The present application composition is directed to a curable composition and utilizing such composition, for example a reversibly crosslinked polysiloxane material with an ethylenically unsaturated monomer to create a formable, shapable, and cuttable localized isolation material for use in dentistry. Not only is the curable composition of the present technology formable, but in some embodiments it is also reformable after it has been cut or torn, in contrast to existing isolation materials such as a rubber sheet. In this regard, the curable composition may be repaired if torn, or the created isolation hole is too large.

Polysiloxane

Generally, the curable composition includes a borate-cross-linked polysiloxane. The borate-cross-linked polysiloxane can, for example, create a barrier, which may assist in repelling moisture, blood, and other contaminants away from the isolated tooth area.

Borate-crosslinked polysiloxanes can be prepared from an appropriately functionalized polysiloxane and a boron-containing cross-linking reagent. In such cases, the boron-containing cross-linking reagent can, for example, form reversible crosslinks in the polysiloxane, which allows tears in the composition to be easily healed or reformed by pressing the composition back together and re-forming a seal.

In some embodiments, the functionalized polysiloxane contains hydroxyl groups, for instance, 2, 3, or more hydroxyl groups which may react with the boron-containing cross-linking reagent. In particular embodiments, the polysiloxane includes two hydroxyl groups. In more particular embodiments, the polysiloxane includes two terminal hydroxyl groups. Boron-containing cross-linking reagents are well known in the art, and include, for example, boric acid, borate esters, and derivatives and combinations thereof. In some embodiments, the boron-containing cross-linking reagent can be of the Formula I:

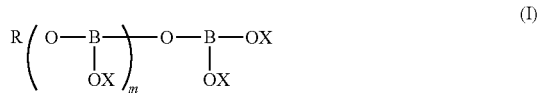

wherein m is an integer from 0 to 3, each R is independently chosen from hydrogen, monovalent hydrocarbon groups, and halogenated monovalent hydrocarbon groups, and each X is independently chosen from hydrogen, monovalent hydrocarbon groups, and halogenated monovalent hydrocarbon groups.

In some such embodiments, each R is independently chosen from hydrogen, aryl groups, halogenated aryl groups, aralkyl groups, aliphatic groups, haloaliphatic groups, and cycloaliphatic groups, and wherein each X is independently chosen from hydrogen, aryl groups, halogenated aryl groups, aralkyl groups, aliphatic groups, haloaliphatic groups, and cycloaliphatic groups. In specific embodiments, each R is independently chosen from hydrogen, phenyl, chlorophenyl, xylyl, tolyl, phenylethyl, benzyl, alkyl, alkenyl, halogenated alkyl, halogenated alkenyl, and cycloalkyl groups. In more specific embodiments, each R is independently chosen from hydrogen and lower alkyl groups.

In some such embodiments of the boron-containing cross-linking reagent, m is zero, each instance of X is hydrogen, and R is hydrogen.

In some embodiments, the borate cross-linked polysiloxane is derived from a poly(dialkylsiloxane) and a boron-containing cross-linking reagent. In some embodiments, the poly(dialkylsiloxane) is a poly(dimethylsiloxane). In some such embodiments, the poly(dimethylsiloxane) is a compound of Formula II:

wherein n is an integer from 10 to 1500, or mixtures thereof. In some embodiments, n is an integer from 10 to 500, in specific embodiments, n is an integer between 10 and 100, for example between 25 and 80.

In any of the foregoing embodiments of the polysiloxane (including those polysiloxanes which include 2, 3, or more hydroxyl groups), the polysiloxane may have a molecular weight of about 500, about 1,000, about 2,000, about 3,000, about 4,000, about 5,000, about 6,000, about 7,000 about, about 8,000, about 9,000, about 10,000, about 25,000, about 50,000, about 75,000, about 100,000, about 150,000, about 200,000, about 250,000, about 300,000, about 350,000, about 400,000 g/mol, or a range between and including any two of these values. For example, the borate-cross-linked polysiloxane may be derived from a bis(hydroxy) terminated polydimethylsiloxane with a molecular weight from about 1,000 g/mol to less than about 50,000 g/mol. In some such embodiments, the borate cross-linked polysiloxane may be derived from a bis(hydroxy) terminated polydimethylsiloxane with a molecular weight from about 5,000 g/mol to about 7,000 g/mol.

In some embodiments, the curable composition includes an excess of borate cross-linking reagent. For example, the curable composition may include unreacted boric acid, borate, borate esters, and derivatives and combinations thereof. In some embodiments, cross-linked polysiloxanes may be prepared, for example, by reacting a polysiloxane with more than a stoichiometric amount of the boron-containing cross-linking reagent. In other embodiments, the borate-crosslinked polysiloxane includes hydroxyl groups. Such cross-linked polysiloxanes may be prepared, for example, by reacting a bis(hydroxyl) terminated polysiloxane with less than a stoichiometric amount of the boron-containing cross-linking reagent.

In some embodiments, the curable composition comprises about 40%, about 50%, about 60%, about 70%, about 80% by weight of borate-crosslinked polysiloxane, or a range between and including any two of these values. In other embodiments, the curable composition comprises greater than about 80% by weight of borate-crosslinked polysiloxane. In some embodiments, the composition includes about 40%, about 50%, about 60%, about 70%, about 80% by weight, or a range between and including any two of these values, of a bis(hydroxyl) terminated polysiloxane where at least of a portion (e.g., 50%, 60%, 70%, 80%, 90%, or substantially all) of the hydroxyl groups are cross-linked with a borate cross-linking reagent. In some such embodiments, substantially all of the hydroxyl groups are cross-linked and the borate cross-linking reagent is present in an excess amount.

Unsaturated Monomer

The curable composition includes at least one ethylenically unsaturated monomer comprising at least two polymerizable groups. In some embodiments, the at least two polymerizable groups can be independently selected at each occurrence from the group consisting of an acrylate, a methacrylate, a vinyl, and an allyl group. In some embodiments, the curable composition includes one or two ethylenically unsaturated monomers, with each monomer independently comprising two, three, or four polymerizable groups.

In some embodiments, the at least one ethylenically unsaturated monomer comprising at least two polymerizable groups can further include a polar functional group, such as a polar group selected from the group consisting of a urethane group, a urea group, a hydroxyl group, or a charged group. In some such embodiments, the at least one ethylenically unsaturated monomer comprising at least two polymerizable groups includes a charged group which is a quaternary ammonium group.

In some embodiments the at least one ethylenically unsaturated monomer comprising at least two polymerizable groups can be an ionic liquid. In some such embodiments, the ionic liquid can be of the Formula III:

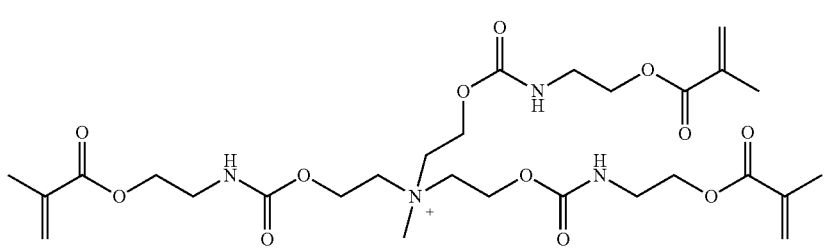

(III)

along with a suitable counter anion, such as for example, methylsulfate (i.e., $^-OSO_2OCH_3$).

In some embodiments, the at least one ethylenically unsaturated monomer comprising at least two polymerizable groups is an optionally substituted polysiloxane. In some such embodiments, the polymerizable groups can be independently selected at each occurrence from the group consisting of an acrylate, a methacrylate, a vinyl, and an allyl group. In some embodiments, the at least one ethylenically unsaturated monomer comprising at least two polymerizable groups is a polysiloxane comprising urea groups and is of the Formula IV:

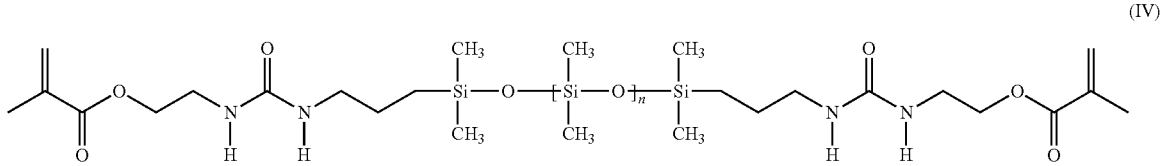

(IV)

wherein n is about 30, about 50, about 70, about 100, about 130, about 160, about 200, about 250, about 300, about 350, about 400, about 450, about 460, about 500, or larger than about 500. In some embodiments of the polysiloxane comprising urea groups, such polysiloxane has a molecular weight of about 3,000 g/mol, about 5,000 g/mol, about 10,000 g/mol, about 14,000 g/mol, about 20,000 g/mol, about 25,000 g/mol, about 30,000 g/mol, about 35,000 g/mol, about 40,000 g/mol, about 41,000 g/mol, about 45,000 g/mol, about 50,000 g/mol, or has a molecular weight of greater than about 50,000 g/mol mol.

Compounds of Formula III and Formula IV may be readily synthesized using procedures described in U.S. Pat. Appl. Pub. No. 2012/0149800 (Lewandowski et al.), WO 92/16593 (Mazurek et al.), U.S. Pat. No. 6,441,118 (Sherman et al.), and U.S. Pat. No. 5,475,124 (Mazurek et al.), or with minor modifications of such procedures.

In some embodiments, the at least one ethylenically unsaturated monomer can include those described in the copending application U.S. Pat. Appl. Ser. No. 62/095,157 (Attorney Docket Number: 75770US002) filed on the same day as the present disclosure. In some embodiments, the at least one ethylenically unsaturated monomer is a polysiloxane comprising urea groups and is of the Formula V:

$$U-[-R^3N-Z-NR^3]-\{-(CO)(CO)-[NH-Y-SiR^1{}_2-(OSiR^1{}_2)_n-OSiR^1{}_2-Y-NH-(CO)(CO)-]_p-[-R^3N-Z-NR^3]-\}_r-U \quad (V)$$

where each $R^1$ is independently an alkyl, haloalkyl, aralkyl, aryl, or aryl substituted with an alkyl, alkoxy, or halo; each Y is independently a divalent alkylene, aralkylene, or a combination thereof; each Z is independently a divalent or higher-valent polydiorganosiloxane alkylene, aralkylene, heteroalkylene, or branched alkylene group; each $R^3$ is hydrogen or alkyl or $R^3$ taken together with Z and with the nitrogen to which they are both attached forms a heterocyclic group; each U is independently a free radically polymerizable group; n is independently an integer of 0 to 1500; p is an integer of 1 or greater; and r is an integer of 1 or greater.

Compounds of Formula V may be readily synthesized using procedures described in the copending application U.S. Pat. Appl. Ser. No. 62/095,157 (Attorney Docket Number: 75770US002) filed on the same day as the present disclosure or with minor modifications of such procedures.

In some embodiments, the curable composition comprises a total of about 25 wt. %, about 30 wt. %, about 35 wt. %, about 40 wt. %, about 45 wt. %, about 50 wt. %, or a range between and including any two of these values, such as, for example, from about 25 wt. % to about 50 wt. % of ethylenically unsaturated monomer(s) comprising at least two polymerizable groups.

In some embodiments, the ethylenically unsaturated monomer comprising at least two polymerizable groups has a molecular weight greater than or equal to: about 300 g/mol, about 400 g/mol, about 500 g/mol, about 1,000 g/mol, about 2,000 g/mol, about 3,000 g/mol, about 4,000 g/mol, about 5,000 g/mol, about 10,000 g/mol, about 25,000 g/mol, about 50,000 g/mol, about 75,000 g/mol, or about 100,000 g/mol.

In some embodiments, the ethylenically unsaturated monomer comprising at least two polymerizable groups has a calculated total solubility parameter of about 10.0 (calories per cubic centimeter)$^{1/2}$, (cal/cc)$^{1/2}$), about 10.1 (cal/cc)$^{1/2}$, about 10.2 (cal/cc)$^{1/2}$, about 10.3 (cal/cc)$^{1/2}$, about 10.4 (cal/cc)$^{1/2}$, about 10.5 (cal/cc)$^{1/2}$, about 10.6 (cal/cc)$^{1/2}$, about 10.7 (cal/cc)$^{1/2}$, about 10.8 (cal/cc)$^{1/2}$, about 10.9 (cal/cc)$^{1/2}$, about 11.0 (cal/cc)$^{1/2}$, about 11.1 (cal/cc)$^{1/2}$, about 11.2 (cal/cc)$^{1/2}$, about 11.3 (cal/cc)$^{1/2}$, about 11.4 (cal/cc)$^{1/2}$, about 11.5 (cal/cc)$^{1/2}$, about 11.6 (cal/cc)$^{1/2}$, about 11.7 (cal/cc)$^{1/2}$, about 11.8 (cal/cc)$^{1/2}$, about 11.9 (cal/cc)$^{1/2}$, about 12.0 (cal/cc)$^{1/2}$, about 12.1 (cal/cc)$^{1/2}$, about 12.2 (cal/cc)$^{1/2}$, about 12.3 (cal/cc)$^{1/2}$, about 12.4 (cal/cc)$^{1/2}$, about 12.5 (cal/cc)$^{1/2}$, about 12.6 (cal/cc)$^{1/2}$, about 12.7 $(cal/cc)^{1/2}$, about 12.8 $(cal/cc)^{1/2}$, about 12.9 $(cal/cc)^{1/2}$, about 13.0 $(cal/cc)^{1/2}$, or a range between and including any two of these values, such as for example from about 10.5 $(cal/cc)^{1/2}$ to about 12.0 $(cal/cc)^{1/2}$.

In some embodiments, the ethylenically unsaturated monomer comprising at least two polymerizable groups has a calculated H-bonding component of greater than or equal to: about 1.0 $(cal/cc)^{1/2}$, about 1.1. $(cal/cc)^{1/2}$, about 1.2 $(cal/cc)^{1/2}$, about 1.4 $(cal/cc)^{1/2}$, about 1.5 $(cal/cc)^{1/2}$, about 1.6 $(cal/cc)^{1/2}$, about 1.8 $(cal/cc)^{1/2}$, about 2.0 $(cal/cc)^{1/2}$, about 2.2 $(cal/cc)^{1/2}$, about 2.4 $(cal/cc)^{1/2}$, about 2.8 $(cal/cc)^{1/2}$, or about 3.0 $(cal/cc)^{1/2}$. In other embodiments, the calculated H-bonding component of the ethylenically unsaturated monomer comprising at least two polymerizable groups is from about 1.5 $(cal/cc)^{1/2}$ to about 3.0 $(cal/cc)^{1/2}$.

Solubility parameters such as calculated total solubility parameters and calculated H-bonding components may be readily computed via molecular dynamics simulations using the general procedures as described by Belmares et al. (Belmares, M.; Blanco, M.; Goddard, W. A.; Ross, R. B.; Caldwell, G; Chou, S. H.; Pham, J.; Olofson, P. M.; Thomas, C.; J. Comp. Chem., 25 (15), 1814 (2004), as implemented in Cerius2 software (Biovia, 5005 Wateridge Vista Drive, San Diego, Calif. 92121 USA) or Culgi software (Culgi Software, Culgi BV, P.O. Box 252, 2300 AG Leiden, The Netherlands). The solubility parameters for a number of exemplary monomers are reported in the Examples, below.

In any of the embodiments of the curable composition disclosed herein, the composition may also include one or more ethylenically unsaturated monomers comprising a single polymerizable group. In some such embodiments, the single polymerizable group of the ethylenically unsaturated monomer or monomers may be independently selected from the group of an acrylate, a methacrylate, a vinyl, and an allyl group. By way of example, the curable composition may include—in addition to the at least one ethylenically unsaturated monomer comprising at least two polymerizable groups—one, two, or three ethylenically unsaturated monomers, each with a single polymerizable group.

In some embodiments, the curable composition includes a total of about 0 wt. %, about 1 wt. %, about 2 wt. %, about 3 wt. %, about 4 wt. %, about 5 wt. %, about 10 wt. %, about 15 wt. %, about 20 wt. %, about 25 wt. %, or a range between and including any two of these values of an ethylenically unsaturated monomer or monomers comprising a single polymerizable group, such as a single acrylate, methacrylate, or vinyl group.

Silane

In some embodiments, the curable composition may optionally include one or more silanes other than the borate-crosslinked polysiloxane (or, as the case may be, other than the borate-crosslinked polysiloxane and the ethylenically unsaturated monomer, where the ethylenically unsaturated monomer is an optionally substituted polysiloxane comprising at least two polymerizable groups). In other embodiments, the silane may be a reactive silane. In some embodiments, the silane may include one or more polymerizable groups, such as an acrylate, a methacrylate, a vinyl, and/or an allyl group. In this regard, such polymerizable groups may be polymerized during curing of the curable composition (e.g., such that they are covalently incorporated into the composition during curing).

In some embodiments, the silane can be an optionally substituted trialkoxysilane. In other embodiments, the trialkoxysilane can include a polymerizable group. In yet other embodiments, the trialkoxysilane can be O-(methacryloxyethyl)-N-(triethoxysilylpropyl)urethane, methacryloxypropyltrimethoxysilane, or combinations thereof.

In some embodiments, the curable composition includes a silane which is unreactive towards any other components in the curable composition, before and/or after curing. In this regard, such an unreactive silane may be considered to be solvent-like. In some such embodiments, the curable composition includes a silane which is unreactive towards one or more hydroxyl groups present on the borate-crosslinked polysiloxane. In some such embodiments, the silane may include one or more polymerizable groups, such as an acrylate, a methacrylate, a vinyl, and/or an allyl group. In some such embodiments, the silane may include 3-methacryloxypropylpentamethyldisiloxane.

In some embodiments, the silane may not react upon curing of the curable composition. In other embodiments, the silane is capable of reacting with one or more hydroxyl groups present on the borate-crosslinked polysiloxane. In some other embodiments, the silane can be covalently bound to the at least one ethylenically unsaturated monomer after curing the curable composition.

In some embodiments, the curable composition comprises about 0.1 wt. %, about 5 wt. %, or from about 0.1 wt. % to about 5 wt. % of silane.

Initiator

In some embodiments, the curable composition can include an initiator system (e.g., one or more initiators) and/or a catalyst that enables the composition to be hardened. In some embodiments, the initiator can be a photoinitiator or a redox initiator. For example, visible and/or near-infrared photoinitiator systems may be used to initiate photopolymerization in compositions including free-radically polymerizable components. For example, a monomer can be combined with a three component or ternary photoinitiator system including a sensitizer, an electron donor, and an iodonium salt as disclosed, for example, in U.S. Pat. No. 5,545,676 (Palazzotto et al.). Alternatively, the composition may include a binary initiator system including a sensitizer (e.g., camphorquinone) and an electron donor (e.g., a secondary or a tertiary alkyl amine compound as disclosed, for example, in U.S. Pat. No. 4,071,424 (Dart et al.)).

Another class of useful photoinitiators includes acylphosphine oxides, as disclosed in European Pat. Publ. No. 173,567 (Ying). Such acylphosphine oxides are of the general formula $(R)_2$—P(O)—CO—R', wherein each R individually can be a hydrocarbyl group (e.g., alkyl, cycloalkyl, aryl, and aralkyl), which may be substituted with a halo-, alkyl- or alkoxy-group, or the two R groups may be joined to form a ring along with the phosphorous atom, and wherein $R^1$ is a hydrocarbyl group, an S—, O—, or N-containing five- or six-membered heterocyclic group, or a —Z—CO—P(O)—$(R)_2$ group, wherein Z represents a divalent hydrocarbyl group (e.g., alkylene or phenylene) having from 2 to 6 carbon atoms.

Acylphosphine oxides useful can include those in which the R and R.sup.1 groups are phenyl or lower alkyl- or lower alkoxy-substituted phenyl. By "lower alkyl" and "lower alkoxy" is meant such groups having from 1 to 4 carbon atoms. The acylphosphine oxide can be bis(2,4,6-trimethylbenzoyl)phenyl phosphine oxide available under the trade designation IRGACURE 819 from Ciba Specialty Chemicals (Tarrytown, N.Y.).

In certain embodiments, the initiator can be a chemical initiator (i.e., initiator system) that can polymerize, cure, or otherwise harden the composition without dependence on irradiation with actinic radiation. The chemically initiator can include redox agents that include an oxidizing agent and a reducing agent. Suitable redox agents are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents can be sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

More than one oxidizing agent or more than one reducing agent may be used. Small quantities of transition metal compounds may also be added to accelerate the rate of redox cure.

In some embodiments, the curable composition comprises about 0.1 wt. %, about 5 wt. %, or from about 0.1 wt. % to about 5 wt. % of initiator.

In some embodiments, the curable composition can be in a two-part system.

Additives

In some embodiments, additives may be incorporated into the curable composition in order to modify the handling characteristics or adjust the patient experience. For example, thickening agents such as fumed silica may be added. Additional additives include de-tackifiers, rheology modifiers, colorants and flavorants. Exemplary de-tackifiers, can include, but are not limited to, fatty acids, oils (mineral and other), or fillers. Exemplary colorants, can include, but are not limited to dyes or pigments.

In some embodiments, the curable composition is prepared by the process of contacting (and optionally mixing to a uniform consistency): a functionalized polysiloxane containing 2, 3, or more hydroxyl groups such as bis(hydroxyl) terminated polydimethylsiloxane (about 40 wt. %, about 50 wt. %, about 60 wt. %, about 70 wt. %, about 80 wt. %, about 90 wt. %, about 95 wt. % or a range between and including any two of these values based on the total weight of the curable composition), a boron-containing cross-linking reagent such as boric acid (about 0.5 wt. %, about 1 wt. %, about 1.5 wt. %, about 2 wt. %, about 3 wt. %, about 4 wt. %, about 5 wt. %, about 6 wt. %, about 7 wt. %, about 8 wt. %, about 9 wt. %, about 10 wt. %, or a range between and including any two of these values based on the total weigh of the curable composition); at least one ethylenically unsaturated monomer comprising at least two polymerizable groups (about 5 wt. %, about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, or a range between and including any two of these values based on the total weight of the curable composition); a silane (0 wt. %, about 0.5 wt. %, about 1 wt. %, about 2 wt. %, about 3 wt. %, about 4 wt. %, about 5 wt. %, or a range between and including any two of these values based on the total weight of the curable composition); an initator or plurality of initiators (about 0.1 wt. %, about 0.5 wt. %, about 1 wt. %, about 2 wt. %, about 3 wt. %, about 4 wt. %, about 5 wt. %, or a range between and including any two of these values based on the total weight of the curable composition); one or more ethylenically unsaturated monomers comprising a single polymerizable group (about 0 wt. %, about 5 wt. %, about 10 wt. %, about 15 wt. %, about 20 wt. %, about 25 wt. %, or a range between and including any two of these values based on the total weight of the composition); and other additives such as detackifiers and/or fillers (0 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt. %, about 20 wt. %, about 25 wt. %, more than about 25 wt. %, or range between and including any two of these values based on the total weight of the curable composition). In some embodiments, about 50%, about 60%, about 70%, about 80%, about 90%, or about 100% of the hydroxyl groups of the functionalized polysiloxane containing 2, 3, or more hydroxyl groups are cross-linked. As will be appreciated by those of skill in the art, the particular amounts of various components of the curable composition can and will vary depending upon the identity of individual components, or compatibility between components.

In any of the aforementioned embodiments of the curable composition, the curable composition may be in the form of a stable mixture. In some embodiments, the curable composition may be a stable heterogeneous mixture.

In other embodiments, for practical reasons, such as when storing the curable composition after its manufacture but prior to its use, it may be desired that the curable composition remain in the form of a homogeneous mixture and not separate into phases (or otherwise become heterogeneous) over time. Thus, in some such embodiments, the curable composition is in the form of a homogeneous mixture which remains homogeneous for a period of at least about 2 days, at least about 3 days, at least about 1 week, at least about 2 weeks, at least about 1 month, at least about 6 months, or at least about 1 year. In such embodiments, the curable composition remains homogeneous at typical storage and/or use temperatures and pressures (e.g., at about 1 atmosphere of pressure and at about 0° C., about 10° C., about 20° C., about room temperature, about 30° C., about 37° C., about 40° C., or a range between and including any two of these temperatures).

Use

Such an isolation material would potentially be simpler to use than existing rubber dental dams. The use of the curable composition of the present application potentially allows the dentist to isolate only a portion of the mouth. In some embodiments, the dentist may be able to avoid using a frame, though the isolation material of the present application may be used with any conventional frame.

Generally, the curable composition is molded into a desired shape. Such molding may be done by hand or by machine. The isolation material may be carved, cut and shaped easily by hand.

In some embodiments, the curable composition can be cured on demand before or after the molding step, or positioning step, or both molding step and the positioning step. After curing, the stiffness of the composition may, for example, increase and the composition may be held in place more firmly. In some embodiments, the curable composition may become more elastic. In some embodiments, the curable composition can be substantially cured less than 5 minutes. In other embodiments, the curable composition can be substantially cured less than 1 minute. In yet other embodiments, the curable composition can be substantially cured less than 30 seconds.

In some embodiments, at least one perforation may be made through the isolation device. Multiple perforations may be made, depending on the needs of the area to be isolated. The isolation device is the positioned inside the patient's mouth to isolate the desired working area through the perforation. In some instances, the edges of the isolation device surrounding the perforation may be pressed around the perforation into the tooth, hard tissue or soft tissue surrounding the area to be isolated, or the working area. The isolation device may also be stretched to conform the isolation device to the soft and/or hard tissue surrounding the working area. The perforation size may be enlarged or manipulated to be smaller, as needed for the working area. In some instances, the isolation device requires no hardware to maintain its place in the patient's mouth.

The isolation material of the present application may also be more comfortable for the patient, and keeps the isolation to only the portion of the mouth that is being repaired.

The following embodiments are intended to be illustrative of the present disclosure and not limiting.

EMBODIMENTS

Embodiment 1 is a curable composition, comprising:
 a borate-crosslinked polysiloxane;
 at least one ethylenically unsaturated monomer comprising at least two polymerizable groups; and
 an initiator.

Embodiment 2 is the curable composition of embodiment 1, further comprising a silane other than the borate-crosslinked polysiloxane.

Embodiment 3 is the curable composition of embodiment 2, wherein the silane is unreactive towards any other components in the curable composition.

Embodiment 4 is the curable composition of embodiment 2, wherein the silane comprises a polymerizable group.

Embodiment 5 is the curable composition of embodiment 4, wherein the polymerizable group is selected from the group consisting of an acrylate, a methacrylate, a vinyl, and an allyl group.

Embodiment 6 is the curable composition of embodiment 2, wherein the silane is a trialkoxysilane.

Embodiment 7 is the curable composition of embodiment 6, wherein the trialkoxysilane is 0-(methacryloxyethyl)-N-(triethoxysilylpropyl)urethane, methacryloxypropyltrimethoxysilane, or combinations thereof.

Embodiment 8 is the curable composition of embodiment 2, wherein the silane does not react towards any other components of the curable composition upon curing of the curable composition.

Embodiment 9 is the curable composition of embodiment 2, wherein the silane is capable of reacting with one or more hydroxyl groups present on the borate-crosslinked polysiloxane.

Embodiment 10 is the curable composition of any of embodiments 1 to 9, wherein the borate-crosslinked polysiloxane comprises hydroxyl groups.

Embodiment 11 is the curable composition of any of embodiments 1 to 10, wherein the borate-crosslinked polysiloxane is derived from a compound of the formula:

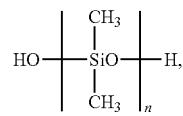

wherein n is an integer from 10 to 1500.

Embodiment 12 is the curable composition of any of embodiments 1 to 11, wherein the borate-crosslinked polysiloxane is derived from poly(dialkylsiloxane) with a molecular weight from about 1,000 g/mol to less than about 50,000 g/mol.

Embodiment 13 is the curable composition of embodiment 12, wherein the poly(dialkylsiloxane) is a poly(dimethylsiloxane).

Embodiment 14 is the curable composition of any of embodiments 1 to 13, wherein the borate-crosslinked polysiloxane is derived from a boron-containing cross-linking reagent selected from the group consisting of boric acid, borate, borate esters, and derivatives and combinations thereof.

Embodiment 15 is the curable composition of embodiment 14, wherein the boron-containing cross-linking reagent is of the formula:

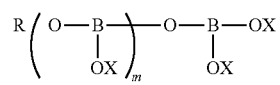

wherein m is an integer from 0 to 3, each R is independently chosen from hydrogen, monovalent hydrocarbon groups, and halogenated monovalent hydrocarbon groups, and each X is independently chosen from hydrogen, monovalent hydrocarbon groups, and halogenated monovalent hydrocarbon groups.

Embodiment 16 is the curable composition of embodiment 15, wherein each R is independently chosen from hydrogen, aryl groups, halogenated aryl groups, aralkyl groups, aliphatic groups, haloaliphatic groups, and cycloaliphatic groups, and wherein each X is independently chosen from hydrogen, aryl groups, halogenated aryl groups, aralkyl groups, aliphatic groups, haloaliphatic groups, and cycloaliphatic groups.

Embodiment 17 is the curable composition of embodiment 15, wherein each R is independently chosen from hydrogen, phenyl, chlorophenyl, xylyl, tolyl, phenylethyl, benzyl, alkyl, alkenyl, halogenated alkyl, halogenated alkenyl, and cycloalkyl groups.

Embodiment 18 is the curable composition of embodiment 15, wherein each R is independently chosen from hydrogen and lower alkyl groups.

Embodiment 19 is the curable composition of any of embodiments 15 to 18, wherein m is zero, each instance of X is hydrogen, and R is hydrogen.

Embodiment 20 is the curable composition of any of embodiments 1 to 19, wherein the polymerizable groups of the at least one ethylenically unsaturated monomer comprising at least two polymerizable groups, are each independently selected from the group consisting of an acrylate, a methacrylate, a vinyl, and an allyl group.

Embodiment 21 is the curable composition of any of embodiments 1 to 20, wherein the at least one ethylenically unsaturated monomer comprises a polar functional group selected from the group consisting of a urethane group, a urea group, a hydroxyl group, or a charged group.

Embodiment 22 is the curable composition of embodiment 21, wherein the charged group is a quaternary ammonium group.

Embodiment 23 is the curable composition of any of embodiments 1 to 20, wherein the at least one ethylenically unsaturated monomer is an optionally substituted polysiloxane comprising at least two polymerizable groups.

Embodiment 24 is the curable composition of any of embodiments 1 to 20, wherein the at least one ethylenically unsaturated monomer is an ionic liquid.

Embodiment 25 is the curable composition of embodiment 24, wherein the ionic liquid is of the formula:

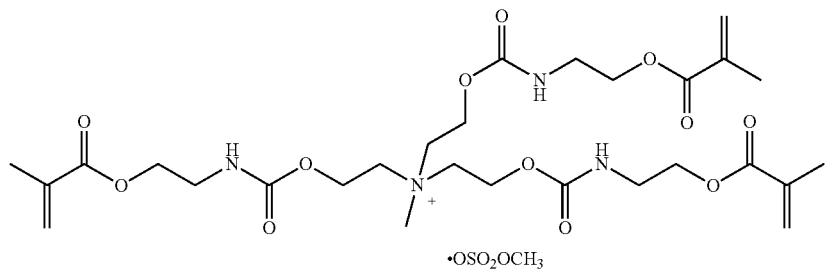

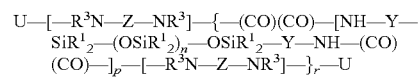

Embodiment 26 is the curable composition of any of embodiments 1 to 25, wherein the at least one ethylenically unsaturated monomer has a calculated total solubility parameter of about 10.5 $(cal/cc)^{1/2}$ to about 12.0 $(cal/cc)^{1/2}$, a calculated H-bonding component of greater than or equal to about 1.2 $(cal/cc)^{1/2}$ and a molecular weight greater than or equal to: about 300 g/mol.

Embodiment 27 is the curable composition of any of embodiments 1 to 26, wherein the curable composition comprises first and second ethylenically unsaturated monomers, the first ethylenically unsaturated monomer comprising two polymerizable groups, the second ethylenically unsaturated monomer comprising one or two polymerizable groups.

Embodiment 28 is the curable composition of any of embodiments 1 to 27, wherein the initiator is a photoinitiator, or a redox initiator.

Embodiment 29 is the curable composition of any of embodiments 1 to 28, further comprising a de-tackifier, a rheology modifier, or combinations thereof.

Embodiment 30 is a method for isolating a working area in a patient's mouth comprising:
  providing the curable composition of any of claims 1 to 29;
  molding the composition to provide a moldable isolation device having a shape;
  positioning the isolation device inside the patient's mouth to isolate the working area; and
  curing the isolation device.

Embodiment 31 is the method of embodiment 30, wherein the moldable isolation device is capable of being molded by hand, by a dental instrument, or a combination thereof.

Embodiment 32 is the method of any of embodiments 30 to 31, further comprising pressing edges of the isolation device around the working area to conform the isolation device to a soft and/or a hard tissue surrounding the working area.

Embodiment 33 is the method of any of embodiments 30 to 32, further comprising stretching the isolation device to conform the isolation device to a soft and/or a hard tissue surrounding the working area.

Embodiment 34 is the method of any of embodiments 30 to 33, wherein the isolation device requires no hardware to maintain its place in the patient's mouth.

Embodiment 35 is the method of any of embodiments 30 to 34, comprising making at least one perforation in the isolation device, wherein the desired working area is within the perforation.

Embodiment 36 is the method of any of embodiments 30 to 35, wherein two or more perforations are made in the isolation device.

Embodiment 37 is the method of any of embodiments 35 to 36, further comprising enlarging or shrinking the size of the perforation on the isolation device to conform the isolation device to a soft and/or hard tissue surrounding the working area.

Embodiment 38 is the curable composition of any of embodiments 1 to 20 and 23, wherein the at least one ethylenically unsaturated monomer comprising at least two polymerizable groups is a compound of the formula:

U—[—$R^3$N—Z—$NR^3$]—{—(CO)(CO)—[NH—Y—SiR$^1_2$—(OSiR$^1_2$)$_n$—OSiR$^1_2$—Y—NH—(CO)(CO)—]$_p$—[—$R^3$N—Z—$NR^3$]—}$_r$—U wherein each $R^1$ is independently an alkyl, haloalkyl, aralkyl, aryl, or aryl substituted with an alkyl, alkoxy, or halo;

each Y is independently a divalent alkylene, aralkylene, or a combination thereof;

each Z is independently a divalent or higher-valent polydiorganosiloxane, alkylene, aralkylene, heteroalkylene, or branched alkylene group;

each $R^3$ is hydrogen or alkyl or $R^3$ taken together with Z and with the nitrogen to which they are both attached forms a heterocyclic group;

each U is independently a free radically polymerizable group;

n is independently an integer of 0 to 1500;
p is an integer of 1 or greater; and
r is an integer of 1 or greater.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis. The materials used to prepare examples of the invention (EX) as well as comparative examples (CE) are outlined below.

In general and as more fully detailed below, curable dental barrier (isolation) materials were prepared from boric acid crosslinked bis-hydroxyl-terminated polydimethylsiloxane (PDMS), an initiator package, and the appropriate ethylenically unsaturated monomer or monomer combination. Additional components, such as silanes (in addition to the borate-crosslinked PDMS) and/or detackifiers, could optionally be included in the curable dental barrier materials. The curable barrier materials may be light and/or chemically (e.g., redox) curable, depending on the specific application. Various factors, including but not limited to: monomer type(s) (e.g., number of polymerizable groups per monomer, monomer molecular weight, monomer polarity including the presence or absence of polar groups, monomer total solubility parameter, monomer H-bonding component, etc.); monomer loading; presence or absence of additives and/or silane(s); and the degree of conversion will influence the properties of the cured barrier materials (e.g., stiffness, stretch properties, deformability, handling properties, etc.).

Examples EX1-EX7 and comparative examples CE1-CE19 were prepared using the following procedure ("General Procedure").

1. Boric Acid Crosslinked Hydroxyl-Terminated PDMS (Component A)

A mixture of ~92 parts hydroxyl-terminated PDMS (bis-hydroxyl terminated, ~5000-7000 MW with a viscosity of 90-120 Centistokes, CAS RN 70131-767-8, available from Gelest, Morrisville, Pa.) was mixed at room temperature under high shear for 3 minutes with ~8 parts boric acid (available from Alfa Aesar, Ward Hill, Mass.). The resulting mixture was heated for 5 hours at 150° C. to provide Component A as a rubbery, shear thickening liquid which was reversibly crosslinked.

2. Silane+Photoinitiator Package (Component B)

A mixture of ~86.5 parts O-(methacryloxyethyl)-N-(triethoxysilylpropyl)urethane (i.e., $H_2C=C(CH_3)C(O)O(CH_2)_2OC(O)N(H)CH_2CH_2CH_2Si(OCH_2CH_3)_3$, "HEMA-urethane silane," available from various suppliers), ~1.5 parts Rhodorsil 2074 (i.e., [(1-methylethyl)phenyl(methylphenyl)iodonium tetrakis(pentafluorophenyl)borate, available from Rhodia), ~2 parts camphorquinone ("CPQ," available from Sigma-Aldrich, St. Louis, Mo.), and ~10 parts ethyl 4-(N,N-dimethylamino)benzoate ("EDMAB," available from Sigma-Aldrich) were mixed together at room temperature until the photoinitiator package components were dissolved in the HEMA-urethane silane. The resultant Component B was provided as a liquid.

3. Component A+Component B (Premixture C)

Component A (95.512 parts) and Component B (4.488 parts) and were mixed with a SPEEDMIXER (FlackTek, Inc., Landrum, S.C.) with heating at 80° C. until the material became stable (Premixture C). Premixture C was provided as a thick, stringy liquid. As detailed more fully below, Premixture C served as a base resin for screening of various ethylenically unsaturated monomers for the preparation and evaluation of light curable barrier materials.

4. Screening of Ethylenically Unsaturated Monomers

The suitability of various ethylenically unsaturated monomers in the preparation of light curable barrier materials was evaluated as follows. A given monomer (~6.5 parts) was added to Premixture C (~12.7 parts), along with stearyl methacrylate (~0.8 parts, available from Sigma-Aldrich). Stearyl methacrylate was added as a de-tackifying agent to improve the handling characteristics of the barrier materials after curing. After mixing at 80° C. to a uniform consistency, the resultant uncured material was visually inspected for phase separation, i.e., whether the monomer was soluble in Premixture C such as to provide a homogeneous material or whether the monomer was partially or fully insoluble in Premixture C such as to give a phase separated material. Homogeneous materials, i.e., those in which the monomer was soluble in Premixture C, were further evaluated to determine whether the material would noticeably cure (and/or thicken) in response to light curing with blue light (20 second exposure using an EPILAR S-10 curing light available from 3M ESPE, St. Paul, Minn.). Screening results of the various ethylenically unsaturated monomers are presented in Table 1.

TABLE 1

Screening of Ethylenically Unsaturated Monomers; Preparation of Curable Barrier Materials.

| Example | Monomer | Monomer Abbreviation | Phase Separation? | Light Curable? |
|---|---|---|---|---|
| EX1 | Dipentaerythritol pentaacrylate (SR-399 from Sartomer, Exton, PA) | — | No | Yes |
| EX2 | Aliphatic urethane dimethacrylate (CN1964 from Sartomer) | UDMA | No | Yes |
| EX3 | Tris(2-hydroxyethyl) isocyanurate triacrylate (SR-368 from Sartomer) | — | No | Yes |
| EX4a EX4b* EX4c* EX4d* | 2,2-Bis[4-(2-hydroxy-3-methacryloyloxypropoxy)-phenyl]propane (available from various suppliers) | BisGMA | No | Yes |
| EX5 | 2-Propenoic acid, 2-methyl-, 1,1'-[1,3-phenylenebis[oxy-2,1-ethanediyloxy[1-(phenoxymethyl)-2,1-ethanediyl]oxycarbonyl- | ERGP-IEM | No | Yes |

TABLE 1-continued

Screening of Ethylenically Unsaturated Monomers; Preparation of Curable Barrier Materials.

| Example | Monomer | Monomer Abbreviation | Phase Separation? | Light Curable? |
|---|---|---|---|---|
| | imino-2,1-ethanediyl]] ester, CAS RN 1353886-10-8 (as further described in U.S. Pat. Appl. Pub. No. 2013/0109777) | | | |
| EX6 | Alpha, omega-dimethacryloxyurea-polydimethylsiloxane, ~5,000 MW (as further described in WO 92/16593) | 5K MAUS | No (thin consistency) | Yes |
| EX7 | N-methyl-2-[[[[2-[(2-methyl-1-oxo-2-propen-1-yl)oxy]ethyl]amino]carbonyl]oxy]-N,N-bis[2-[[[[2-[(2-methyl-1-oxo-2-propen-1-yl)oxy]ethyl]amino]carbonyl]oxy]ethyl]ethanaminium methylsulfate (1:1), CAS RN 1270041-82-1 (as further described in U.S. Pat. Appl. Pub. No. 2012/0149800) | Quat-22 | No | Yes |
| CE1 | Glycerol 1,3-dimethacrylate (available from various suppliers) | GDMA | No (thin consistency) | No |
| CE2 | Neopentylglycol dimethacrylate (available from various suppliers) | — | No (thin consistency) | No |
| CE3 | (2-Hydroxyethyl) methacrylate (available from various suppliers) | HEMA | No (thin consistency) | No |
| CE4 | Trimethylolpropane triacrylate (SR-351H from Sartomer) | — | Yes | Not tested |
| CE5 | Trimethylolpropane trimethacrylate (SR-350 from Sartomer) | — | Yes | Not tested |
| CE6 | Pentaerythritol triacrylate (SR-444 from Sartomer) | — | Yes | Not tested |
| CE7 | Pentaerythritol tetraacrylate (SR-295 from Sartomer) | — | Yes | Not tested |
| CE8 | 2-Phenoxyethyl acrylate (SR-339 from Sartomer) | — | Yes | Not tested |
| CE9 | 2-Phenoxyethyl methacrylate (SR-340 from Sartomer) | — | Yes | Not tested |
| CE10 | Ethoxylated (3) trimethylolpropane triacrylate (SR-454 from Sartomer) | — | Yes | Not tested |
| CE11 | Ethoxylated (4) pentaerythritol tetraacrylate (SR-494 from Sartomer) | — | Yes | Not tested |
| CE12 | Tricyclo[5.2.1.0$^{2,6}$]decanedimethanol diacrylate (from Sigma-Aldrich) | — | Yes | Not tested |
| CE13 | Dodecanediol dimethacrylate (available from various suppliers) | DDDMA | Yes | Not tested |
| CE14 | Poly(propyleneglycol) dimethacrylate 425 (~660 MW, Polysciences, Warrington, PA)) | PPGDMA | Yes | Not tested |
| CE15 | Triethyleneglycol dimethacrylate (available from various suppliers) | TEGDMA | Yes | Not tested |
| CE16 | Ethoxylated bisphenol A methacrylate, 6 moles ethylene oxide (as further described in U.S. Pat. No. 6,030,606, available from Sartomer as "CD541") | BisEMA-6 | Yes | Not tested |
| CE17 | Ethoxylated bisphenol A methacrylate, 2 moles ethylene oxide | BisEMA-2 | Yes | Not tested |
| CE18 | Poly(ethylene glycol) dimethacrylate, ~600 MW (available from various suppliers) | PEG600 DM | Yes | Not tested |
| CE19 | Bisphenol A, bis(3-methacryloyloxypropyl) ether (also referred to as 2-propenoic acid, 2-methyl-, 1,1'-[(1-methylethylidene)bis(4,1-phenyleneoxy-3,1-propanediyl)] ester), [27689-12-9] (available from various suppliers) | PROCRYLATK | Yes | Not tested |

*Examples EX4b, EX4c, and EX4d were prepared in an analogous fashion to EX4a, except that ~0.8 parts of a de-tackifying agent other than stearyl methacrylate was used. EX4b employed mineral oil, EX4c employed Nujol, and EX4d employed paraffin as de-tackifying agents.

From the Table 1, it is apparent that the monomers in Examples EX1-EX7 were miscible in Premixture C (and in particular miscible with the borate cross-linked PDMS) to provide stable barrier materials which were light-curable. In general, the uncured barrier materials could be stretched, torn, and reformed. Upon light curing, the barrier materials noticeably stiffened and increased in modulus, evidencing irreversible crosslinking. While monomers in Comparative Examples CE1-CE3 were also miscible in Premixture C, such materials were not light curable. In the case of Comparative Examples CE4-CE19, the monomers were not appreciably miscible in Premixture C. Thus, it is apparent that not all ethylenically unsaturated monomers can provide light-curable barrier materials.

Ethylenically Unsaturated Monomer Combinations

As shown in Table 2, combinations of ethylenically unsaturated monomers could be used to prepare light curable barrier materials. Notably, the addition of BisGMA to systems which were otherwise uncurable (cf. CE1 and CE2 in Table 1) provided barrier materials which could be light cured, like examples EX1-EX7. The barrier materials in Table 2 were prepared according to the General Procedure.

TABLE 2

Light Curable Barrier Materials with Ethylenically Unsaturated Monomer Combinations.

| Example | Monomers/Monomer Abbreviations | Phase Separation? | Light Curable? |
|---|---|---|---|
| EX8 | GDMA:BisGMA (50:50) | No | Yes |
| EX9 | Neopentylglycol dimethacrylate:BisGMA (50:50) | No | Yes |

Silane Effects

In each instance for Examples EX1-EX9, the light curable barrier formulations included HEMA-urethane-silane. Additional experiments were performed to evaluate the effect of removing HEMA-urethane-silane from the formulation (EX10-EX13) or substituting HEMA-urethane-silane with a different silane material altogether (EX14).

1. Removal of HEMA-Urethane-Silane (EX10-EX13)

A light curable barrier material, EX10, with a similar formulation as EX6 but lacking HEMA-urethane-silane, was prepared as follows. 5K MAUS (5.2501 parts), CPQ (0.013 parts), EDMAB (0.0508 parts), Rhodorsil 2074 (0.0188 parts), stearyl methacrylate (0.9043 parts), and Component A (8.7723 parts) were mixed at 80° C. to a uniform consistency. The resultant uncured barrier material did not phase separate. The uncured material could be stretched, torn, and reformed. Upon light curing, the barrier material stiffened and increased in modulus. Thus, this material behaved similarly to that of EX6.

Other light curable barrier materials lacking HEMA-urethane-silane in their respective formulations were also prepared, using different monomer systems (EX11-EX13). The various monomers employed for EX10-EX13 and the associated performance results are presented in Table 3, below. Examples EX11-EX12 were prepared by mixing CPQ (~0.022-0.024 parts), EDMAB (~0.10-0.11 parts), and indicated monomer (~9.88-9.93 parts) at ~80-100° C. to prepare a premixture. This premixture (~3.50 parts) was then speed-mixed with stearyl methacrylate (~0.40-0.41 parts) and Component A (~6.10 parts) at 80° C. EX13 was prepared in a similar fashion by mixing CPQ (0.0220 parts), EDMAB (0.1085 parts), and the indicated monomer (9.878 parts, further described below) at ~80-100° C. to prepare a premixture. This premixture (3.5014 parts) was then speed-mixed with stearyl methacrylate (0.4078 parts) and Component A (6.1039 parts) at 80° C. As shown in Table 3, EX10-EX13 provided light curable barrier materials which noticeably stiffened upon exposure to blue light.

TABLE 3

Light Curable Barrier Materials Lacking HEMA-Urethane-Silane.

| Example | Monomer | Monomer Abbreviation | Phase Separation? | Light Curable? |
|---|---|---|---|---|
| EX10 | Alpha, omega-dimethacryloxy-urea-polydimethylsiloxane, ~5,000 MW (as further described in WO 92/16593) | 5K MAUS | No | Yes |
| EX11 | Alpha, omega-dimethacryloxy-urea-polydimethylsiloxane, ~14,000 MW (readily prepared with minor modifications to those described in WO 92/16593) | 14K MAUS | No | Yes |
| EX12 | Alpha, omega-dimethacryloxy-urea-polydimethylsiloxane, ~14,000 MW (readily prepared with minor modifications to those described in WO 92/16593) | 41K MAUS | No | Yes |
| EX13 | Alpha, omega methacrylated oxamido siloxane | Monomer 1 | No | Yes |

Monomer 1 (a compound of Formula V) used in EX13, was prepared as follows. A 2-liter, 3-necked reaction vessel equipped with a mechanical stirrer, vacuum adapter and a thermometer was charged with approximately 1000 grams of 14K PDMS diamine (a polydimethylsiloxane diamine prepared as described in U.S. Pat. No. 6,534,615 with an amine equivalent weight (AEW) of 6,007 grams/equivalent as measured by titration). With stirring and under a reduced pressure (<1 torr), the vessel was heated to >150° C. with a hot air gun for >10 minutes until bubbles were no longer generated. The heat was removed and the flask allowed to cool to <60° C. under vacuum. The flask was back-filled with dry nitrogen. From the vessel was poured 307.41 grams ($5.12 \times 10^{-2}$ eq.) of the 14K PDMS diamine into a flame-dried 1 quart, clear jar. To the 14K PDMS diamine was added 192.41 grams ($3.41 \times 10^{-2}$ eq.) of a 14K dioxamido ester (a polydimethylsiloxane dioxamido ester prepared as described in preparative example 1 of U.S. Pat. No. 7,501,184 with an equivalent weight of 5640 grams/equivalent as determined by titration). The jar was capped and placed on a roller mill for 5 days. The AEW of the diamine oligomer was determined to be approximately 34,410 grams/equivalent by titration. The diamine oligomer was methacrylated with IEM (2-isocyanatoethyl methacrylate, available from various suppliers) as follows. A flame-dried, 250 mL amber jar was charged with 42.01 grams ($1.22 \times 10^{-3}$ eq.) of the diamine oligomer, 22.1 grams of dry THF, and 0.209 grams ($1.35 \times 10^{-3}$ eq.) of IEM. The jar was capped, shaken vigorously to combine, and placed on a roller mill. After 24 hours, a small aliquot was removed and the THF removed under reduced pressure. Analysis by 1H-NMR showed no methylene protons for a primary amine. Monomer 1 was obtained by removing THF at ~60° C. The structure of Monomer 1 is represented below.

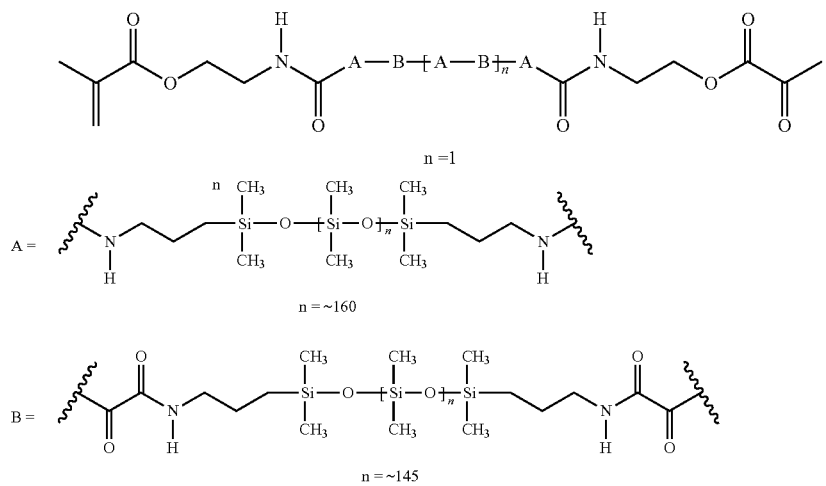

2. Substituting HEMA-Urethane-Silane with a Different Silane (EX14)

A light curable barrier material with a formulation similar to that of EX4a (which included BisGMA as the monomer), but using 3-methacryloxypropylpentamethyldisiloxane in place of HEMA-urethane-silane, was prepared as follows. 3-Methacryloxypropylpentamethyldisiloxane (4.4 parts, available from various suppliers), CPQ (0.11 parts), and EDMAB (0.5 parts) were mixed at 80° C. until uniform ("Component C"). Component A (19 parts) as previously described was mixed with Component C (1 part) at 80° C. to provide Component D. Component D (6.43 parts), Bis-GMA (3.3 parts) and stearyl methacrylate (0.42 parts) were then mixed together at 80° C. until uniform. The resultant uncured barrier material did not phase separate and could be stretched, torn, and reformed by hand. Upon light curing, the barrier material stiffened and increased in modulus.

Consistency Evaluation of Curable Barrier Materials

Stable uncured barrier materials which were susceptible to light curing (i.e., EX1-EX14) were evaluated after 2-3 days for changes in consistency and/or phase separation. Advantageously, a number of the uncured barrier materials exhibited good shelf-life, remaining stable after several days while retaining good handling properties (particularly EX3, EX4a, EX4b, and EX7).

For barrier materials EX1-EX14, consistency changes arising from light curing were evaluated in the following fashion. For each uncured barrier material, a 0.5 gram (g) sample was formed into a ball. The ball was sandwiched between upper and lower glass slides and a weight (913 g) was applied to the upper slide for a period of 2 minutes, during which time the ball deformed into a disc. The diameter of the disc was then measured in inches. A similar test procedure was employed for cured barrier materials. In particular, a 0.5 g sample of uncured barrier material was formed into a ball which was then irradiated for a period of 1 minute with an EPILAR S-10 curing light. The sample was allowed to post-cure for a period of 2 minutes. The ball was then sandwiched between glass slides, the weight (913 g) was applied to the upper slide for a period of 2 minutes, and the diameter of the resultant disc was measured. Consistency test results for the uncured and cured barrier materials are summarized in Table 4.

TABLE 4

Consistency Evaluation

| Example | Uncured Diameter (In) | Cured Diameter (In) | Difference (In) |
|---|---|---|---|
| EX1 | 1.344 | 0.875 | 0.469 |
| EX2 | 1.573 | 0.802 | 0.771 |
| EX3 | 1.000 | 0.531 | 0.469 |
| EX4a | 1.125 | 0.729 | 0.396 |
| EX4b | 1.1146 | 0.7604 | 0.354 |
| EX4c | 1.031 | 0.635 | 0.396 |
| EX4d | 1.115 | 0.646 | 0.469 |
| EX5 | 1.365 | 1.052 | 0.313 |
| EX6 | 2.198 | 0.771 | 1.427 |
| EX7 | 1.1563 | 0.9375 | 0.219 |
| EX8 | 1.1042 | 0.8125 | 0.292 |
| EX9 | 2.2604 | 0.8646 | 1.396 |
| EX10 | 1.2916 | 0.6354 | 0.656 |
| EX11 | 1.333 | 0.75 | 0.583 |
| EX12 | 1.3125 | 0.6458 | 0.667 |
| EX13 | 0.95833 | 0.8333 | 0.125 |
| EX14 | 1.125 | 0.4375 | 0.688 |

The results in Table 4 illustrate that, in each instance for EX1-EX14, the cured barrier material was less deformable in comparison to the uncured barrier material.

Molecular Dynamics Studies of Ethylenically Unsaturated Monomers

Typically, it is preferable that the uncured barrier material is substantially homogeneous, such that after curing, the resultant cured barrier material is also substantially homogeneous. In this regard, properties such as moldability and/or tearabilty are largely the same throughout the bulk of the barrier material (either in a cured or uncured state). The various components of the uncured barrier material should be reasonably compatible with one another, such that phase separation does not occur to an appreciable amount. For instance, in uncured barrier materials which include significant portions of an ethylenically unsaturated monomer (or monomers) and borate cross-linked PDMS, the ethylenically unsaturated monomer(s) should be reasonable compatible (e.g., soluble) with the borate cross-linked PDMS.

Computational molecular dynamics simulations were performed to calculate solubility parameters such as the total solubility parameter and the simulated H-bonding component for selected ethylenically unsaturated monomers in Table 1. The simulations were performed using the general procedures as described by Belmares et al. (Belmares, M.; Blanco, M.; Goddard, W. A.; Ross, R. B.; Caldwell, G; Chou, S. H.; Pham, J.; Olofson, P. M.; Thomas, C.; J. Comp. Chem., 25 (15), 1814 (2004), as implemented in Cerius2 software (Biovia, 5005 Wateridge Vista Drive, San Diego, Calif. 92121 USA) or Culgi software (Culgi Software, Culgi BV, P.O. Box 252,2300 AG Leiden, The Netherlands). The results are presented in Table 5.

TABLE 5

Molecular Dynamics Calculations.

| Monomer | Example | Monomer Molecular Weight (g/mol) | Total Solubility Parameter $((cal/cc)^{1/2})$ | Simulated H-Bonding Component $((cal/cc)^{1/2})$ |
|---|---|---|---|---|
| Dipentaerythritol pentaacrylate | EX1 | 525 | 10.59 | 1.47 |
| UDMA | EX2 | 471 | 11.45 | 2.29 |
| Tris(2-hydroxyethyl) isocyanurate triacrylate | EX3 | 423 | 11.71 | 0.00 |
| BisGMA | EX4a-EX4d, EX8, EX9 | 513 | 10.96 | 2.18 |
| ERGP-IEM | EX5 | 809 | 10.52 | 1.28 |
| GDMA | CE1 | 228 | 11.71 | 2.52 |
| Neopentylglycol dimethacrylate | CE2 | 240 | 9.67 | 0.00 |
| HEMA | CE3 | 130 | 13.80 | 3.30 |
| Trimethylolpropane triacrylate | CE4 | 296 | 9.46 | 0.00 |
| Trimethylolpropane trimethacrylate | CE5 | 338 | 9.28 | 0.00 |
| Pentaerythritol triacrylate | CE6 | 298 | 10.91 | 2.21 |
| 2-Phenoxyethyl acrylate | CE8 | 192 | 10.90 | 0.00 |
| Ethoxylated (3) trimethylolpropane triacrylate | CE10 | ~645 | 10.35 | 0.00 |
| Ethoxylated (4) pentaerythritol tetraacrylate | CE11 | >>300 | 11.02 | 0.00 |
| Tricyclo[5.2.1.0$^{2,6}$]decanedimethanol diacrylate | CE12 | 304 | 10.12 | 0.00 |
| DDDMA | CE13 | 310 | 9.40 | 0.00 |
| TEGDMA | CE15 | 286 | 10.17 | 0.00 |
| BisEMA-2 | CE17 | >>300 | 10.26 | 0.00 |

The results in Table 5, along with results from Tables 1-3, help to rationalize the types of ethylenically unsaturated monomers which work well in the present barrier materials, i.e., those which not only provide a homogenous barrier material, but also provide a homogeneous barrier material which can be cured. In general, at least one ethylenically unsaturated monomer which includes at least two polymerizable groups is needed in the barrier composition. From Table 5, it is apparent that to provide a homogeneous barrier material, the monomer with multiple polymerizable groups generally possesses: a molecular weight greater than or equal to 300 g/mol; a total solubility parameter of about 10.5 $(cal/cc)^{1/2}$ to about 12.0 $(cal/cc)^{1/2}$; an H-bonding component of greater than or equal to 1.2 $(cal/cc)^{1/2}$; a heterocyclic core; or a combination of two or more of these characteristics. For example, difunctional monomers with a total solubility parameter of about 10.5 $(cal/cc)^{1/2}$ to about 12.0 $(cal/cc)^{1/2}$; and either:

(i) a molecular weight greater than or equal to 300 g/mol and an H-bonding component of greater than or equal to 1.2 $(cal/cc)^{1/2}$ (e.g., EX1-EX2, EX4-EX5, and EX8-EX9); or (ii) a heterocyclic core (e.g., isocyanurate core-containing EX3) gave rise to homogeneous barrier materials, while those that did not meet these criteria did not.

Identification of an Ethylenically Unsaturated Monomer Via Molecular Dynamics Calculations (EX15)

Molecular dynamics calculations on the diacrylate ester of bisphenol A epoxy resin (~500 MW) indicated a total solubility parameter of 10.90 $(cal/cc)^{1/2}$ and H-bonding component of 2.20 $(cal/cc)^{1/2}$. Subsequent to the calculation, a light curable barrier material derived from this difunctional monomer was prepared as follows. 3-Methacryloxypropyl-trimethoxysilane (8.80 parts, available from various suppliers), CPQ (0.22 parts), and EDMAB (1.00 parts) were mixed at 80° C. until uniform ("Component G"). Component A (9.51 parts) as previously described was mixed with Component G (0.47 part) at 80° C. to provide Component H. Component H (6.1 parts), the diacrylate ester of bisphenol A epoxy resin (3.5 parts, available from Allnex USA Inc., Alpharetta, Ga. as Ebecryl 600), and stearyl methacrylate (0.4 parts) were then mixed together at 80° C. until uniform. The resultant uncured barrier material did not phase separate and could be stretched, torn, and reformed by hand. Upon light curing, the barrier material stiffened and increased in modulus. Consistency testing was performed in the manner previously described (uncured diameter: 1.4270 inches; cured diameter: 0.9791 inches; difference: 0.4479 inches).

Preparation of Redox-Curable Barrier Material (EX16)

A two-part redox curable barrier material was prepared as follows. The first part of the two-part mixture was prepared by first mixing HEMA-urethane silane (4.2930 parts) with 4-tert-butyl-N,N-dimethylaniline (0.7086 parts, available from Sigma-Aldrich) until the aniline derivative was dissolved. A portion of this mixture (0.2892 parts) was then mixed with ERGP-IEM (3.1520 parts), stearyl methacrylate (0.6014 parts), and Component A' (5.9647 parts) at 80° C. with a SPEEDMIXER to provide the first part of the two-part redox curable barrier material (Paste 1). Component A' was identical to Component A as previously described, except that the boric acid crosslinked hydroxyl-terminated PDMS was heated for 3 hours (rather than 5 hours).

The second part of the two-part redox curable barrier material (Paste 2), was prepared by first mixing HEMA-urethane silane (4.2903 parts) with cumene hydroperoxide (0.7023 parts, available from Alfa Aesar) until the cumene hydroperoxide was completely dissolved. A portion of this mixture (0.2817 parts) was then mixed with ERGP-IEM (3.1582 parts), stearyl methacrylate (0.6003 parts), and Component A' (5.9647 parts) at 80° C. with a SPEEDMIXER to provide Paste 2.

Approximately equal parts of Paste 1 and Paste 2 were then kneaded together by hand. The resultant material noticeably stiffened and displayed reduced stretchability, evidencing redox polymerization.

TABLE 6

Summary of Weight Percent Formulations of Curable Barrier Materials EX1-EX16.

| Example | Hydroxyl-terminated PDMS | Boric Acid | Monomer(s) | Silane | Detackifier | Rhodorsil 2074 | EDMAB | CPQ |
|---|---|---|---|---|---|---|---|---|
| EX1 | 55.798 | 4.852 | 32.500 | 2.465 | 4.000 | 0.043 | 0.285 | 0.057 |
| EX2 | 55.798 | 4.852 | 32.500 | 2.465 | 4.000 | 0.043 | 0.285 | 0.057 |
| EX3 | 55.798 | 4.852 | 32.500 | 2.465 | 4.000 | 0.043 | 0.285 | 0.057 |
| EX4a | 55.798 | 4.852 | 32.500 | 2.465 | 4.000 | 0.043 | 0.285 | 0.057 |
| EX4b | 55.798 | 4.852 | 32.500 | 2.465 | 4.000 | 0.043 | 0.285 | 0.057 |
| EX4c | 55.798 | 4.852 | 32.500 | 2.465 | 4.000 | 0.043 | 0.285 | 0.057 |
| EX4d | 55.798 | 4.852 | 32.500 | 2.465 | 4.000 | 0.043 | 0.285 | 0.057 |
| EX5 | 55.798 | 4.852 | 32.500 | 2.465 | 4.000 | 0.043 | 0.285 | 0.057 |
| EX6 | 55.798 | 4.852 | 32.500 | 2.465 | 4.000 | 0.043 | 0.285 | 0.057 |
| EX7 | 55.798 | 4.852 | 32.500 | 2.465 | 4.000 | 0.043 | 0.285 | 0.057 |
| E8 | 55.798 | 4.852 | 32.500 | 2.465 | 4.000 | 0.043 | 0.285 | 0.057 |
| EX9 | 55.798 | 4.852 | 32.500 | 2.465 | 4.000 | 0.043 | 0.285 | 0.057 |
| EX10 | 53.770 | 4.676 | 34.979 | 0.000 | 6.025 | 0.125 | 0.338 | 0.087 |
| EX11 | 56.105 | 4.879 | 34.522 | 0.000 | 4.046 | 0.000 | 0.370 | 0.079 |
| EX12 | 56.111 | 4.879 | 34.575 | 0.000 | 4.001 | 0.000 | 0.354 | 0.080 |
| EX13 | 56.083 | 4.877 | 34.512 | 0.000 | 4.073 | 0.000 | 0.379 | 0.077 |
| EX14 | 55.368 | 4.815 | 32.512 | 2.782 | 4.138 | 0.000 | 0.316 | 0.070 |
| EX15 | 53.477 | 4.650 | 35.000 | 2.523 | 4.000 | 0.000 | 0.287 | 0.063 |
| EX16 | 54.842 | 4.769 | 31.532 | 2.450 | 6.005 | | 0.403* | |

*Redox couple total: 4-tert-butyl-N,N-dimethylaniline (0.205 wt. %) & cumene hydroperoxide (0.198 wt. %)

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A curable composition, comprising:
    a borate-crosslinked polysiloxane;
    at least one ethylenically unsaturated monomer comprising at least two polymerizable groups; and
    an initiator.

2. The curable composition of claim 1, further comprising a silane other than the borate-crosslinked polysiloxane.

3. The curable composition of claim 2, wherein the silane is unreactive towards any other components in the curable composition.

4. The curable composition of claim 2, wherein the silane comprises a polymerizable group selected from the group consisting of an acrylate, a methacrylate, a vinyl, and an allyl group.

5. The curable composition of claim 2, wherein the silane is a trialkoxysilane.

6. The curable composition of claim 5, wherein the trialkoxysilane is O-(methacryloxyethyl)-N-(triethoxysilylpropyl)urethane, methacryloxypropyltrimethoxysilane, or combinations thereof.

7. The curable composition of claim 2, wherein the silane does not react towards any other components of the curable composition upon curing of the curable composition.

8. The curable composition of claim 2, wherein the silane is capable of reacting with one or more hydroxyl groups present on the borate-crosslinked polysiloxane.

9. The curable composition of claim 1, wherein the borate-crosslinked polysiloxane comprises hydroxyl groups.

10. The curable composition of claim 1, wherein the borate-crosslinked polysiloxane is derived from poly(dialkylsiloxane) with a molecular weight from about 1,000 g/mol to less than about 50,000 g/mol.

11. The curable composition of claim 1, wherein the borate-crosslinked polysiloxane is derived from a boron-containing cross-linking reagent selected from the group consisting of boric acid, borate, borate esters, and derivatives and combinations thereof.

12. The curable composition of claim 1, wherein the polymerizable groups of the at least one ethylenically unsaturated monomer comprising at least two polymerizable groups, are each independently selected from the group consisting of an acrylate, a methacrylate, a vinyl, and an allyl group.

13. The curable composition of claim 1, wherein the at least one ethylenically unsaturated monomer comprises a polar functional group selected from the group consisting of a urethane group, a urea group, a hydroxyl group, or a charged group.

14. The curable composition of claim 13, wherein the charged group is a quaternary ammonium group.

15. The curable composition of claim 1, wherein the at least one ethylenically unsaturated monomer is a substituted or unsubstituted polysiloxane comprising at least two polymerizable groups.

16. The curable composition of claim 1, wherein the at least one ethylenically unsaturated monomer is an ionic liquid.

17. The curable composition of claim 1, wherein the at least one ethylenically unsaturated monomer has a calculated total solubility parameter of about 10.5 $(cal/cc)^{1/2}$ to about 12.0 $(cal/cc)^{1/2}$, a calculated H-bonding component of greater than or equal to about 1.2 $(cal/cc)^{1/2}$ and a molecular weight greater than or equal to about 300 g/mol.

18. The curable composition of claim 1, wherein the curable composition comprises a first and a second ethylenically unsaturated monomer, the first ethylenically unsaturated monomer comprising two polymerizable groups, the second ethylenically unsaturated monomer comprising one or two polymerizable groups.

19. A method for isolating a working area in a patient's mouth comprising:
providing the curable composition of claim 1,
molding the composition to provide a moldable isolation device having a shape;
positioning the isolation device inside the patient's mouth to isolate the working area; and
curing the isolation device.

20. The curable composition of claim 1, wherein the at least one ethylenically unsaturated monomer comprising at least two polymerizable groups is a compound of the formula:

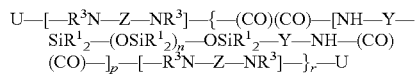

wherein each $R^1$ is independently an alkyl, haloalkyl, aralkyl, aryl, or aryl substituted with an alkyl, alkoxy, or halo;
each Y is independently a divalent alkylene, aralkylene, or a combination thereof;
each Z is independently a divalent or higher-valent polydiorganosiloxane, alkylene, aralkylene, heteroalkylene, or branched alkylene group;
each $R^3$ is hydrogen or alkyl or $R^3$ taken together with Z and with the nitrogen to which they are both attached forms a heterocyclic group;
each U is independently a free radically polymerizable group;
n is independently an integer of 0 to 1500;
p is an integer of 1 or greater; and
r is an integer of 1 or greater.

* * * * *